United States Patent [19]

Sorger

[11] Patent Number: 4,582,064
[45] Date of Patent: Apr. 15, 1986

[54] METHOD AND APPARATUS FOR DETERMINING $pO_2$ HISTOGRAMS

[75] Inventor: Peter Sorger, Münster, Fed. Rep. of Germany

[73] Assignee: Wolfgang Fleckenstein, Rondeshagen, Fed. Rep. of Germany

[21] Appl. No.: 606,835

[22] Filed: Apr. 24, 1984

[30] Foreign Application Priority Data

Sep. 1, 1982 [DE] Fed. Rep. of Germany ....... 3232455
Sep. 1, 1983 [EP] European Pat. Off. ........ 83108631.9
Sep. 1, 1983 [WO] PCT Int'l Appl. ............ EP83/00231

[51] Int. Cl.$^4$ .............................................. A61B 5/00
[52] U.S. Cl. .................................................. 128/635
[58] Field of Search .................. 128/632, 635; 204/403

[56] References Cited

U.S. PATENT DOCUMENTS

| | | | |
|---|---|---|---|
| 3,098,813 | 7/1963 | Beebe et al. | 128/635 X |
| 3,224,436 | 12/1965 | Massena | 128/635 |
| 4,154,228 | 5/1979 | Feldstein et al. | 128/329 R |
| 4,294,258 | 10/1981 | Bernard | 128/635 |
| 4,445,515 | 5/1984 | Diresta | 128/635 X |

FOREIGN PATENT DOCUMENTS 2943958  5/1981  Fed. Rep. of Germany.

OTHER PUBLICATIONS

Ehrly & Schroeder, "Oxygen Pressure in Ischemic Muscle Tissue of Patients with Chronic Occlusive Arterial Diseases", *Angiology*, vol. 28, No. 2 (1977).

Spence & Walker, "Measurement of Oxygen Tension in Human Skin", *Medical and Biological Engineering*, vol. 14, No. 2 (Mar. 1976).

"Grundlagen und Bedeutung der lokalen Sauerstoffdruckmessung und des $pO_2$ Histograms für die Beurteilung der Sauerstoffversorgung der Organe und des Organismus" by D. W. Lübbers.

*Primary Examiner*—John F. Niebling
*Assistant Examiner*—Nam X. Nguyen
*Attorney, Agent, or Firm*—Walter C. Farley

[57] ABSTRACT

Apparatus for the determination of $pO_2$-histograms by means of a needle probe.

The apparatus for the determination of $pO_2$-histograms in living tissue comprises a macro needle probe of larger diameter moved stepwise between individual measurement locations, the step widths being in the order of magnitude of the probe diameter and the speed being considerably higher than $pO_2$-changes within the tissue. Measured values are determined shortly after the probe has come to a standstill. Thus, disturbances in the tissue $pO_2$ due to compression effects induced by the thick probe do not falsify the measured value although a thick and stable probe is used. A polarographic measuring site with a ring-shaped metal film electrode used here is characterized especially by a recessed metal ring electrode. By this means a measuring site of low stirring effect and very short response time is obtained.

9 Claims, 11 Drawing Figures

METHOD AND APPARATUS FOR DETERMINING PO₂ HISTOGRAMS

This invention relates to an apparatus for the determination of pO₂-histograms by means of a needle probe which carries a measuring site and is incrementally moved to successive measuring locations.

BACKGROUND OF THE INVENTION

For the state of the art in this technology, please refer to D. W. Lübber's article "Grundlagen und Bedeutung der lokalen Sauerstoffdruckmessung und des pO₂ Histograms für die Beurteilung der Sauerstoffversorgung der Organe und des Organismus" in A. M. Ehrly "Messung des Gewebesauerstoffdruckes bein Patienten", publishing house Gerhard Witzstock, 1981, pages 11–18. According to the article the prior art is the following:

Reliable statements on the oxygen supply of the tissue which are usable for medical diagnoses can only be determined via the determination of the statistical distribution of local oxygen-pressures in the tissue. In order to do so, the local oxygen pressure (pO₂) has to be determined for a large number of measuring locations (usually at least 100).

The statistical evaluation of these measured values results in a so-called pO₂-histogram which provides in a diagram a diagnostically usable statement on the current oxygen supply conditions. There is an example on page 15 of the mentioned article.

According to the above-mentioned article, an apparatus of the kind mentioned at the beginning is well-known using—according to page 14, middle of right column—probe tip diameters of less than 1 μm. According to page 16, third paragraph, however, work with such micro probes involves major problems.

The disadvantages of micro probes can be mostly attributed to the danger of breaking. For this reason, they can be only used in highly specialized scientific laboratories and not in the clinic routine.

Furthermore, on page 16, third paragraph, there are mentioned unbreakable thicker probes imbedded in metal cannulas. But the latter are said to register unreliable measured values, most likely due to a local impact on the blood circulation. Thus, these unbreakable probes cannot be used for the relevant purposes.

SUMMARY OF THE INVENTION

An object of the invention is to create an apparatus of the kind mentioned at the beginning, providing reliable results and guaranteing a tolerable work effort for clinical use.

In accordance with the invention this and other objects are achieved by means of an apparatus in which a needle probe has a measuring site near its tip and a diameter of at least 10 microns. An incremental drive is provided to axially advance the needle in steps to successively position the site at individual measuring locations, each step being a distance greater than the distance between the probe tip and the measuring site plus a tissue-dependent amount in the order of magnitude of the probe diameter. The drive moves the tip through each step in a time which is less than the average time constant of the pO₂ decrease in the interstitial tissue after interruption of the oxygen supply. A signal evaluation apparatus evaluates the measurement at each location and produces a display signal. The evaluation apparatus and measuring site together have a time constant which is at least thirty times smaller than the average time constant of the pO₂ decrease and produces a display signal at a time between about three times the apparatus time constant and 0.1 times the average time constant.

In accordance with the invention a stable, unbreakable and therefore easily handled probe is used whose diameter is larger than that of the micro probe by at least one order of magnitude. The invention is based on the discovery that the oxygen pressure at the measurement location decreases after such a thick probe has punctured the tissue all the way to a measurement location. This fact can be explained by compression of the surrounding tissue caused by the thick probe. The considerably thinner micro probes naturally do not bring about this effect (their diameter being less than 1 μm). The range of influence surrounding the probe where the pO₂ decreases, depends on the type of tissue (which can be determined by experiments) as well as on the diameter of the probe. For that reason, the probe is always shifted between two measurement locations in such a way that the probe's measuring site gets to a location still uninfluenced by the previous position. Furthermore, the invention is based on the discovery that the pO₂ decrease caused by the probe takes place at a speed which is dependent on the place in the tissue. The average oxygen-pressure-decrease time constant $\tau_g$ is tissue-specific and can be determined. If the probe is moved quickly enough, uninfluenced measurement locations are always reached where the true pO₂ can be determined shortly after the probe has come to a standstill. Accordingly, the probe's signal response time has to be short in order to determine the uninfluenced original pO₂-value before there is a pO₂ change due to the probe itself. In fact the real pO₂ of the tissue can be determined if the ratio of the apparatus's response time constant to the changing time constant of the tissue pO₂ is properly established and measurement takes place right after the response time interval of the probe. This had not been deemed possible according to the prior art.

The measuring site of the probe can function in accordance with a suitable physical principle, for example in accordance with an optical method using light conductors or in accordance with a well-known polarographic method. In the latter case interferences can occur when the probe is moved, which do, however, die down within the reaction time of the probe after the probe has come to a standstill and no longer disturb measurement at the time when the measured value is determined. Thus, the invention has provided apparatus which allows the precise determination of the real tissue-pO₂ and thus the construction of an informative pO₂-histogram, the probe structure being rugged and suitable for routine application. The apparatus according to the invention allows an extremely fast determination of values for a complete histogram at the required, about 100, measurement locations which can be determined for example within approximately two minutes as a result of its handy application and the permissible fast step sequence. This high and so far unsurpassed measuring speed is a further pre-condition for successful clinical application.

A further advantage results from providing a time constant ratio $\tau_g/\tau_v$ of more than 100 in accordance with the invention. With such a low time-constant of the apparatus response, the measured value can be determined even faster and thus more precisely corresponding to the undisturbed tissu-pO₂.

Furthermore, an apparatus in accordance with the invention preferably has a distal-end probe diameter larger than 100 microns. Beginning with about this diameter range, the probe can be produced particularly easily and in a manner furnishing a stable measured value.

An apparatus in accordance with the invention also can have the measuring site attached in the precision ground opening of a metal cannula.

In this way, the probe can be manufactured easily, with the mechanical stability and particularly the breaking strength being very high.

Further in accordance with the invention, a probe type with a polarographic measuring site turned out to be extremely suitable for the applicant and is particularly marked by low production costs and a clinically-advantageous disposable use. Due to the small active metal surface, the polarographic data are favorable.

A polarographic macro probe which can be easily used for the previously mentioned purposes, has a film on a fiber core surrounded by a casting compound. The use of a casting compound permits a cost-effective production, especially when the site is in a cannula.

The metal-film surface is favorably arranged in a recess of the precision ground surface. By this means, the reproducible production of probes capable of stable measurement and with uniform polarographic data is made possible, which are particularly marked by extremely short response times necessary for the invention-conformable use with a time constant of markedly less than one second.

A probe having a diameter between about 200 to 500 microns and a set width of about 400 microns, a $\tau_v$ value of less than 150 milliseconds and able to determine a measured value not later than 1.5 seconds after movement is especially suitable for routine checks in a patient's skeletal muscles, e.g. for checking a so-called smoker's leg.

For claims 6 and 7, protection is claimed even independently of claim 1 to 5 and 8.

BRIEF DESCRIPTION OF THE DRAWINGS

In the drawings the invention is described schematically and by way of example. The drawings present:

FIG. 2b: A sectional view according to line 200 in FIG. 2a.

FIG. 1 shows a schematic and total presentation of an apparatus in accordance with the invention in clinical application.

Figure 1:
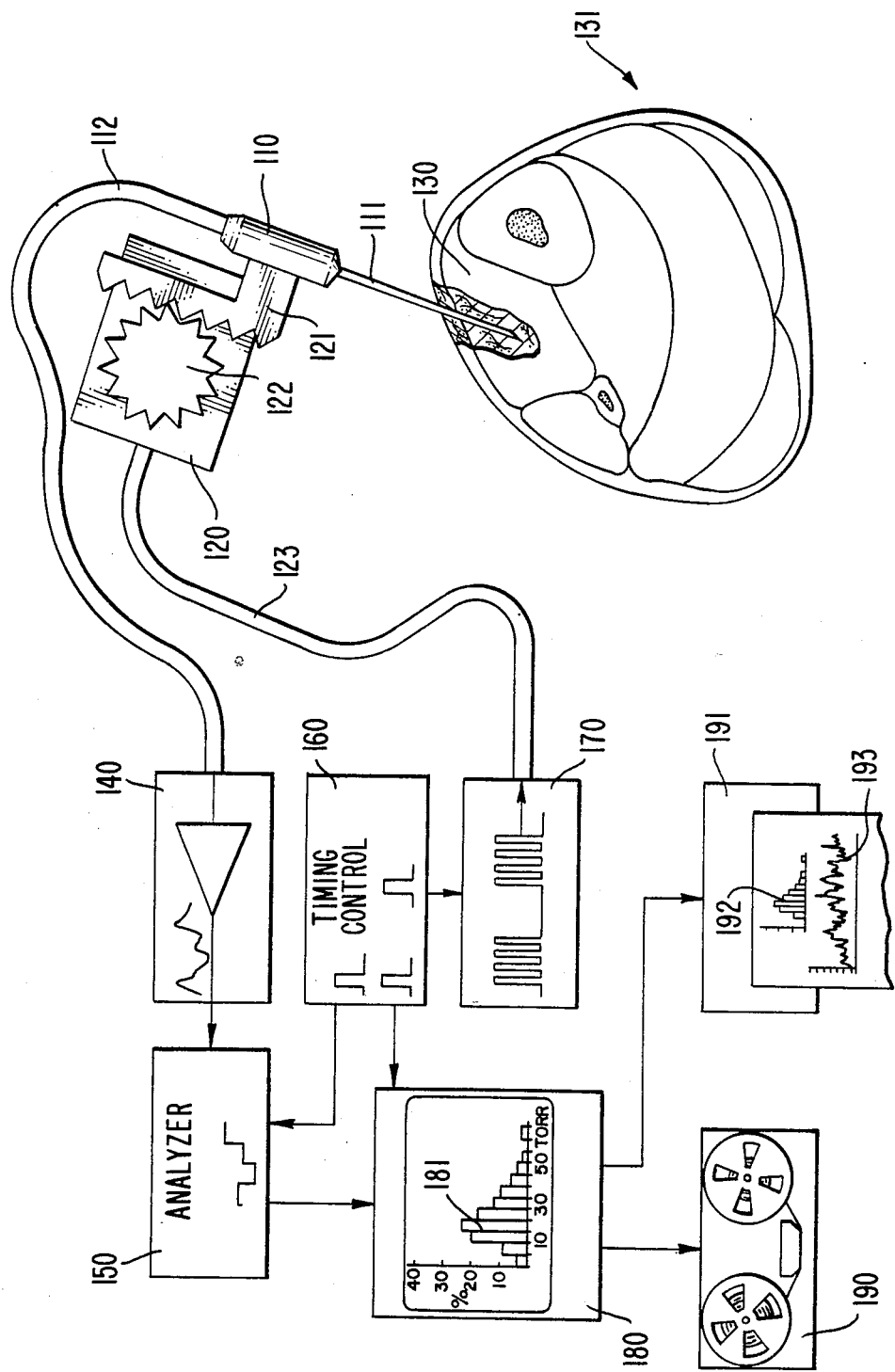
FIG. 1: The schematic total presentation of an apparatus according to the invention.

A probe 111 is fastened to a probe carrier 110. The polarographic measuring site installed in the probe tip is connected to a measuring signal evaluation device via a probe-connecting cable 112 as illustrated in the block diagram.

A probe drive 120 arranged stationary, for example fastened to a tripod not shown, drives the probe carrier 110 in the axial direction of the probe 111 by means of an electronically controlled motor. In the example given here, this is schematically illustrated with rack 121 and pinion 122. A connection cable 123 provides for energy supply and control of the drive 120.

FIG. 1 illustrates a typical application for clinical diagnostics. The probe 111 has punctured the musculus tibialis anterior 130 of a human lower leg 131 the sectional view of which is depicted in the diagram.

The measuring signal evaluation device represented in the block diagram of FIG. 1 is equipped with a signal amplifier 140 connected to the measuring site of the probe via a cable 112. The device transmits the amplified signal to a unit 150 for the determination of the real tissue $pO_2$, the unit 150 being controlled by a time control 160.

Furthermore, the time control sends control pulses to a motor-drive control 170 which is connected to the drive 120 via a cable 123 and to a histogram calculator 180 having a viewing screen 181 for the illustration of the calculated histogram. The computer 180 also controls a data storage unit 190 and a data printer 191 which can—depending on the design of the computer 180—print out the histogram 192 and, if necessary, an illustration 193 of the $pO_2$—profile in the traversed tissue on the represented paper strip.

Figure 2A:
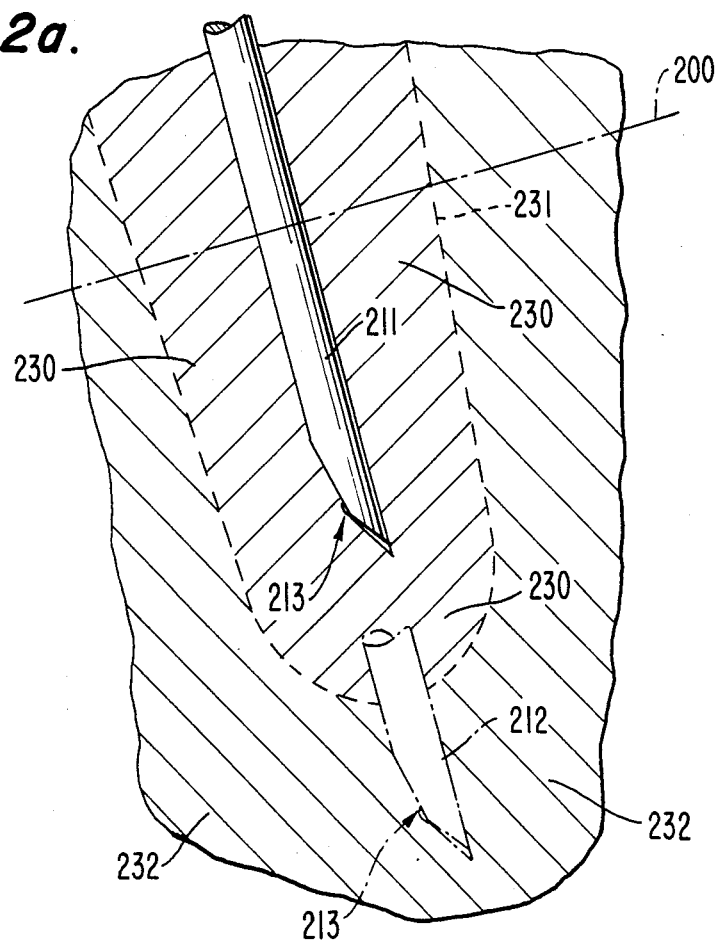
FIG. 2a: A sectional view along the probe axis through a measurement location in the tissue.

FIG. 2a shows the greatly magnified tip of the probe 111 in a position 211 and in a position 212 advanced by one step of the drive 120. The illustration of FIG. 2a shows a probe arranged inside of a metal cannula having the typical tip precision ground surface of a thin metal cannula whose outer diameter amounts to some multiples of 100 $\mu$m. 213 is the measuring site on the precision ground surface of the cannula.

The illustration of FIG. 2a shows the probe tip having punctured the tissue depicted in hatching. A probe in accordance with the invention having a diameter of more than 10 $\mu$m—preferably more than 100 $\mu$m and up to about 500 $\mu$m—affects the adjacent tissue in a compression zone 230 by displacement and compression, the tissue 232 outside of the boundary 231 being left unaffected by compression. The compression area 230 has a radius which is in the order of magnitude of the probe diameter. The compression area radius in FIG. 2a amounts to about three times the probe diameter.

The compression area radius depends on the compression sensitivity of the specific tissue examined and can be determined for any type of tissue and made available to the physician in the form of a table.

Figure 2B:
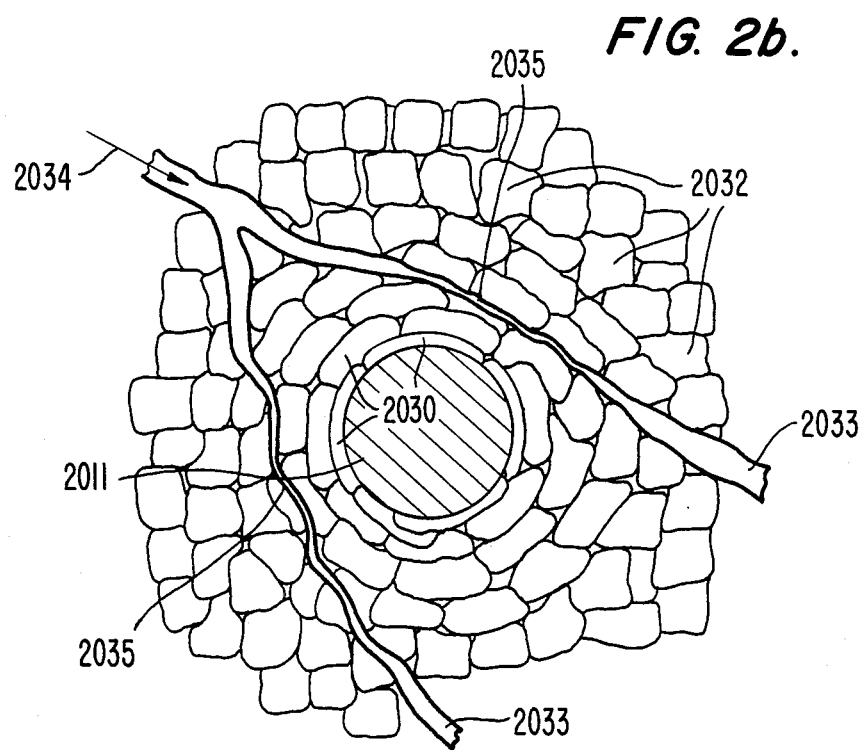

FIG. 2b shows a sectional view that is perpendicular to the illustration of FIG. 2a 2011 illustrates the probe in cross section at section line 200 in FIG. 2a. 2030 illustrates tissue cells that were severely deformed and bruised by compression in compression area 230. Tissue cells 2032 beyond the compression area, that is beyond the threshold 231, are not compressed. Blood flow 2034 that supplies the tissue, flows through blood vessels 2033 whose cross section has become smaller in the compression area 230 as depicted in FIG. 2b. *This means that the blood supply and thus oxygen supply is reduced in compression area 2035 by reduction of the diameter of blood vessels.*

After the probe tip has punctured position 211 (FIG. 2a), the oxygen pressure in compression area 230 decreases. For that reason, the step width between two measurement locations has to be large enough to provide such a step between the measurement location at the position of the probe tip 211 and the next measurement location in position 212, to get the measuring site 213 out of the compression area 230 being the result of the previous position 211. The step width has to amount to the radius of the compression area at least. If the measuring site 213 is far behind the probe tip, this distance must be added to the step width. The step width depends on the compression-area radius—which in turn is dependent on the diameter of the probe and on the structure of the type of tissue concerned.

In the skeletal muscles of a patient as for example in the case of application explained in FIG. 1, a step width of more than 800 μm is necessary, if the probe diameter amounts to about 200–500 μm, if the injection angle is less than 45° to the longitudinal axis of muscle fibers and if the probe tip geometry is in accordance with FIG. 2a.

FIGS. 3a through 3e show the time course of parameters above time axis t as the abscissa. Within period $T_1$, the probe tip is located at a measurement location, for example according to position 211 (FIG. 2a). Within period $T_2$, the probe moves from one measurement location to the next. At $T_2$, $T_4$, $T_5$ the probe has reached the next measurement location (212 according to FIG. 2a).

Figure 3A:
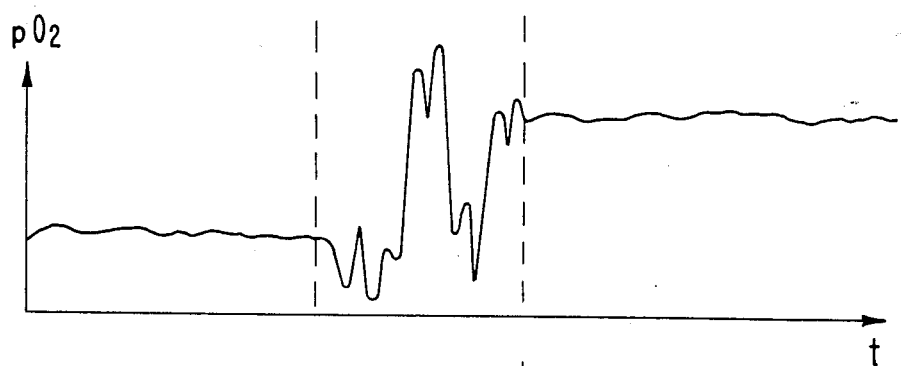
FIG. 3a to 3e: The time-depending variations of parameters vertically arranged for the purpose of explaining the generation of the signal of the probe's measuring site as represented in FIG. 3e.

The oxygen-pressure values ($pO_2$) are shown in FIG. 3a, which, corresponding to the real $pO_2$-values, could at best be determined with an ideal probe, for instance with a micro probe that exerts compression effects to the tissue. At the first measurement location at $T_1$ a certain $pO_2$ is measured. During step time $T_2$, areas of different oxygen pressures are met and a new $pO_2$-value is reached at $T_3$, $T_4$, $T_5$. Before and after each step movement, the $pO_2$-values remain constant.

Figure 3B:
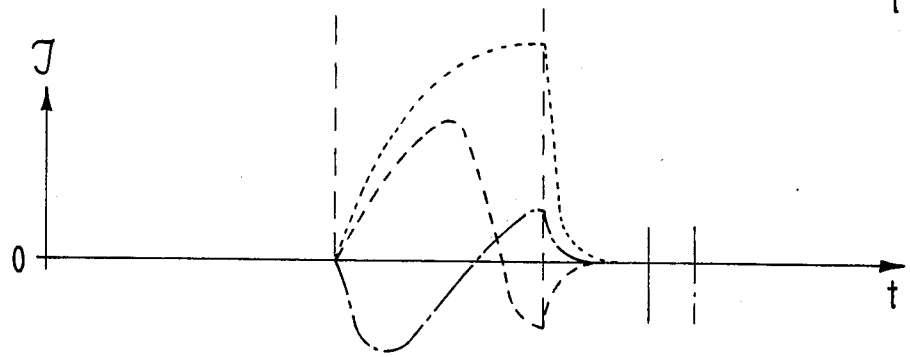

FIG. 3b shows disturbing effects in three different and typical examples which occur during the movements of polarographic probes, that is within $T_2$, and die down soon after the probe has come to a standstill. This is based on the assumption that the probe is displaced in an area with a constant $pO_{2l}$. *The disturbing signal is shown as part I of the measured-value of the polarographic current.*

Figure 3C:
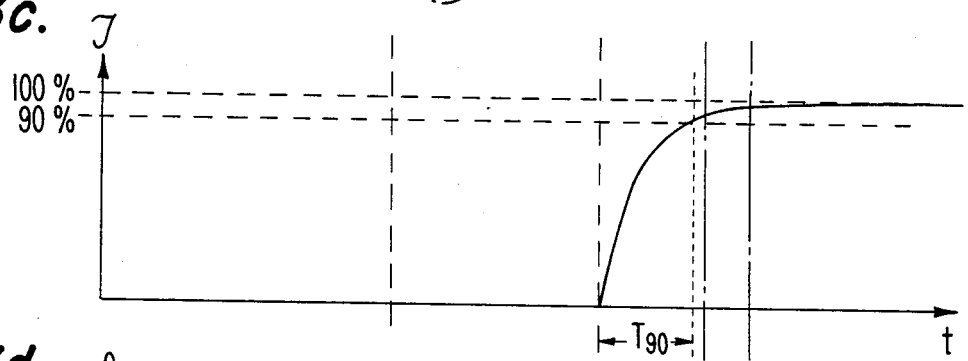

FIG. 3c illustrates the response of the equipment which is largely determined by its slowest component, the measuring site 213. Current signal I of the measuring site is shown at the beginning of $T_3$ after a $pO_2$-step from 0 to 100%. The equipment registers 90% of the real value after a time $T_{90}$. This corresponds to about $3\tau_v$, $\tau_v$ being the time constant of the apparatus's response time.

Figure 3D:
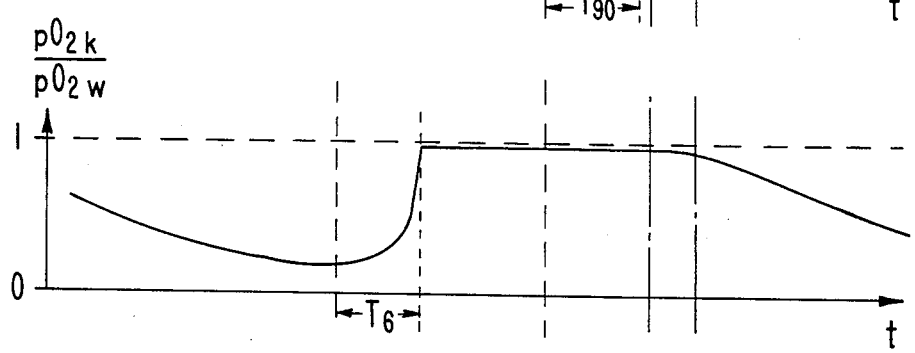

FIG. 3d shows the oxygen decrease in the compression area 230 surrounding the probe tip, which is caused by the compression effect (FIG. 2a). Here, you will find illustrated the ratio of the oxygen pressure $pO_{2k}$, disturbed by compression, to the undisturbed and real $pO_{2w}$. Upon the beginning of step time $T_2$, the measuring site leaves the compression area 230 at about end of $T_6$ and passes through undisturbed tissue areas untill the end of step time $T_2$. When the probe has come to a standstill at the next measurement location, that is at the beginning of $T_3$, the oxygen pressure begins to decrease again in the area of the probe tip due to compression. The oxygen pressure decrease has a time constant $\tau_g$ corresponding to the negative slope in the area of $T_3$, $T_4$, $T_5$. The decrease is slight at first and then more significant so that the real $pO_2$-value is still available at the beginning of the decrease in the curve ($pO_{2k}/pO_{2w}$ just about equals 1). FIG. 3d is once again based on the assumption that the probe passes through areas with equal oxygen pressure.

Figure 3E:
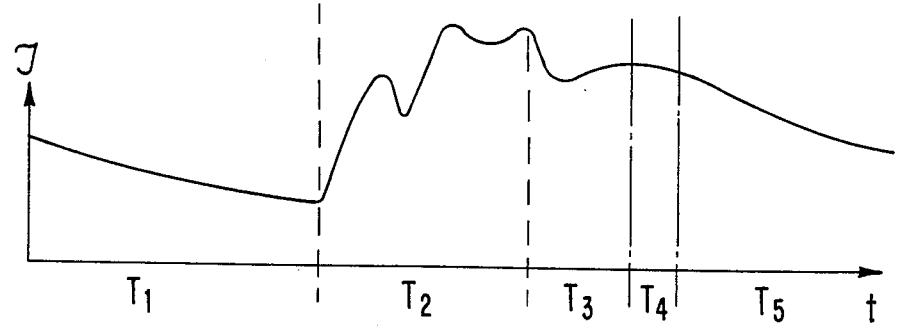

An example of a real signal (polarographic current I) is represented in FIG. 3e. This course is essentially the result of overlapping effects according to FIGS. 3b, 3c, and 3d. The decreasing section of the compression curve according to FIG. 3d can be seen within the range of $T_1$. The step range $T_2$ is essentially determined by speed-dependent disturbing effects shown in FIG. 3b and the local oxygen differences shown in FIG. 3a.

After the probe has come to a standstill at the beginning of $T_3$, the decline of the disturbing effects in accordance with diagram 3b and the probe response in accordance with FIG. 3c can be seen. In the range of $T_4$, the signal essentially corresponds to the real and undisturbed tissue-$pO_2$ whereas it is decreasing in the range of $T_5$ (as with $T_1$).

In the range of $T_4$, the disturbing effects have declined in accordance with FIG. 3b. The probe has passed its response time $T_{90}$ according to FIG. 3c and displays nearly 100%. According to FIG. 3d, the oxygen pressure has not yet decreased substantially by tissue compression. For that reason, the range of $T_4$ can be used as a measuring window for the determination of a measured value which corresponds to the real oxygen pressure at the measurement location and can be used for the drawing up of the histogram.

Figure 4:
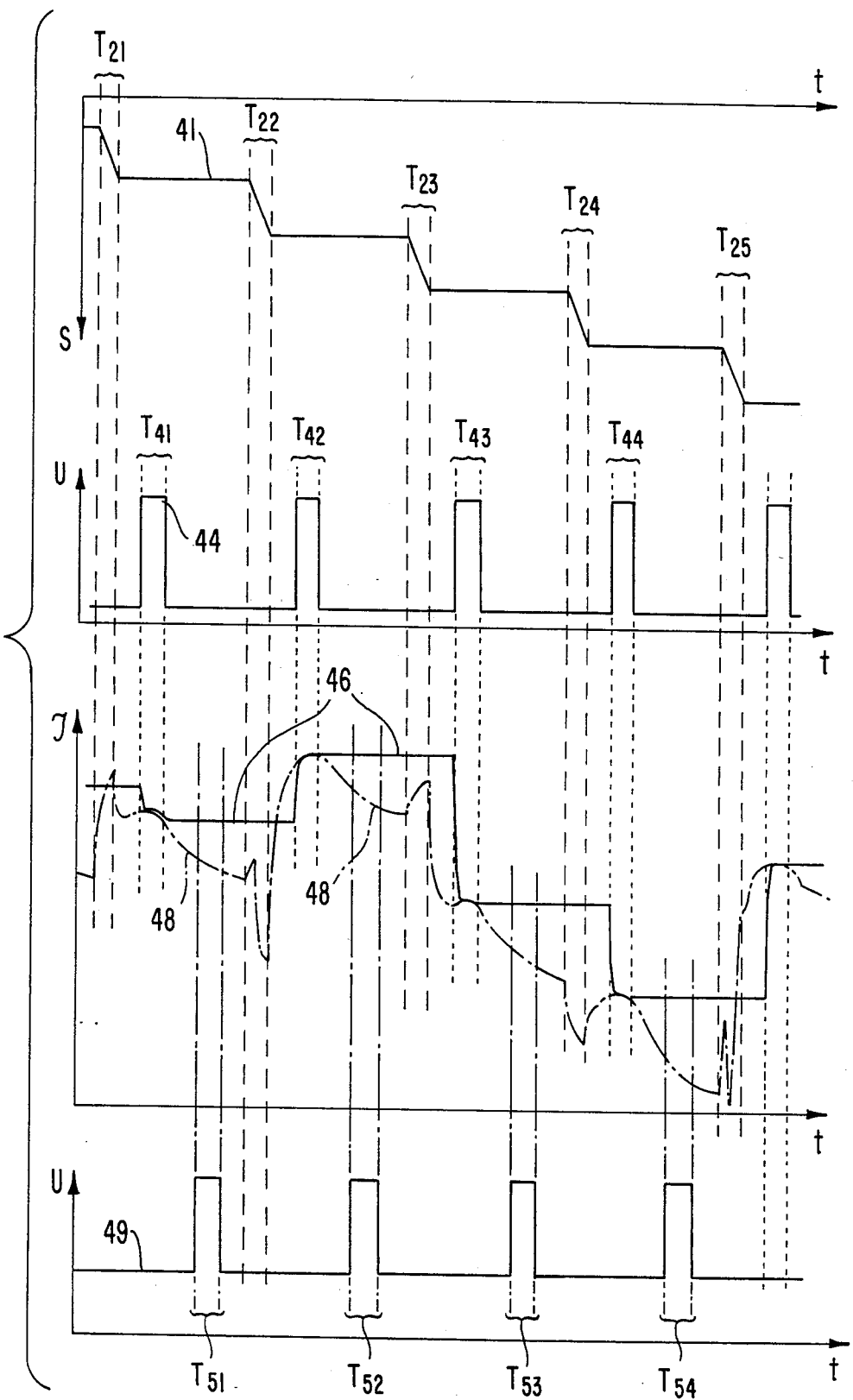
FIG. 4: Various control sequences of the equipment of FIG. 1 in vertically synchronized arrangement with respect to the measuring signal.

FIG. 4 shows the course of time of pulses within the measuring signal evaluation device of FIG. 1, being controlled by the time control 160 by means of corresponding pulses. Several parameters are shown in synchronized vertical arrangement over time axis t.

The path S of the probe drive is given on the uppermost diagram. The locus 41 of the probe tip shows the dwelling time and the moving time. Diagram I (polarographic current) shows the real signal 48 according to FIG. 3e. FIG. 4 illustrates five consecutive steps, different $pO_2$ values being determined at the individual measurement locations. Curve 44 shows the output voltage U of the time control 160 which is fed into the equipment 150 for the evaluation of the signal. By the gate pulses 44, a measuring window is opened during $T_4$ (FIG. 3e).

The measuring signal curve 48 shows the typical course, according to FIG. 3e, for the area comprising step times $T_{21}$ to $T_{25}$. Between these, $pO_2$-decreases caused by tissue compression are found as in the $T_1$ and $T_5$-range of FIG. 3e. The measuring window control pulses of control signal 44 are at $T_{41}$ to $T_{45}$. A stepshaped signal 46 can be registered at the output of equipment 150 for the determination of the real tissue $pO_2$ signal 46 remains constant from one measuring window to the next and always corresponds to the previously determined value measured at a measurement location. The transmission of these values to the computer 180, necessary for the determination of the histogram, takes place at $T_{51}$, $T_{52}$, $T_{53}$ and $T_{54}$ by control pulses 49 from the time control 160 to the equipment 150.

In the following a few terms used above will be explained in detail:

The literature reports driving speeds of less than 100 μm per minute for micro probes used for the purposes mentioned above. Using small micro probes without compression effects, such slow driving speeds are possible. It is essential to realize that thick probes used according to the invention bring about compression effects leading to a pO$_2$-decrease within the surrounding tissue. This takes place at an average time constant $\tau_g$. If the probe is moved too slowly, measuring site 213 never leaves the compressed area 230 spreading around the probe tip. The advancing speed must be higher than the decreasing speed of the tissue-pO$_2$ by at least one to two orders of magnitude. For that reason, the step time T$_2$ must amount to less than one tenth $\tau_g$ or—even better—to less than one hundredth $\tau_g$.

As for FIG. 3d, one further comment should be made: T$_6$ is magnified considerably for the purpose of better graphical illustration. Furthermore, it has to be mentioned that the tissue-pO$_2$ does not decrease right after the probe has come to a standstill but remains constant for some time (about T$_3$) before it begins to decrease. This may be caused by oxygen storage within the tissue.

Movement speeds of the probe used according to the invention amount to e.g. 600000 $\mu$m per minute, more than three orders of magnitude faster than known from the state of the art.

As for the tissue pO$_2$-decreasing speed, marked above by the time constant $\tau_g$, it has to be added that $\tau_g$ may vary markedly depending on the respective micro structure of the tissue. In the description above, $\tau_g$ always represents the mean value to be determined tissue-specifically. If the pO$_2$-value is determined not less than one tenth of $\tau_g$ after the probe has come to a standstill, only a few measurement locations considerably faster pO$_2$-decreasing times are found leading to distortions of the measured valued in there places. The number of incorrect measured values then amounts to less than 1% which does not have significant negative effect on the statistical evaluation of the pO$_2$-histogram.

In the following, an embodiment of the probe 111 being well suitable for the apparatus according to the invention is described. This embodiment of the probe, however, is not limited to the illustrated case of application of the macro probe, but also suitable for micro probes with a much smaller diameter and for other probe types—as for example tissue surface probes—due to the design of the polarographically active measuring site described above.

Figure 5:
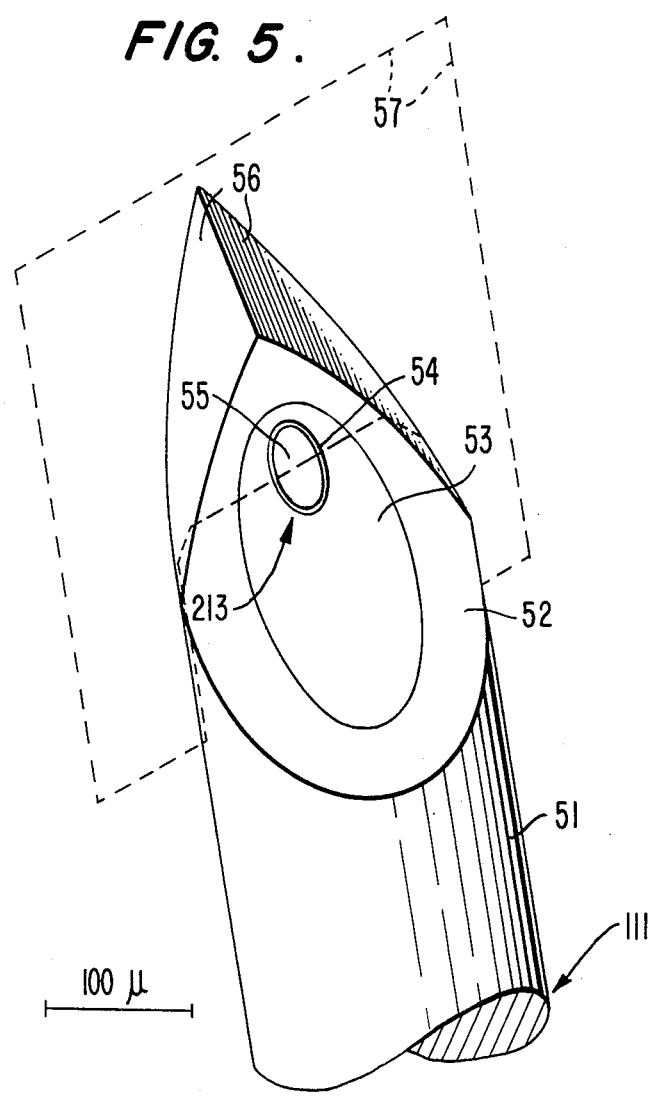
FIG. 5: A perspective view of the probe's measuring site.

FIG. 5 perspectively shows the tip of probe 111 of FIG. 1 and 2a.

A steel tube 51 having a ground tip is used e.g. in the form of a commercial syringe cannula having a outer diameter in the range of a few 100 $\mu$m. The ground surface has a main grounded surface 52 and lancet ground surfaces 56 and is therefore suitable for puncturing the tissue to be examined, without damaging it.

Measuring site 213 having the form of a polarographic measuring site in the described embodiment, is equipped with an electrode ring 54 being located in the area of the precision ground surface 52 and surrounding an insulating body 55. Outside of the electrode ring 54 the space inside of the steel coating 51 is filled with an electrical insulating casting compound 53.

Figure 6:
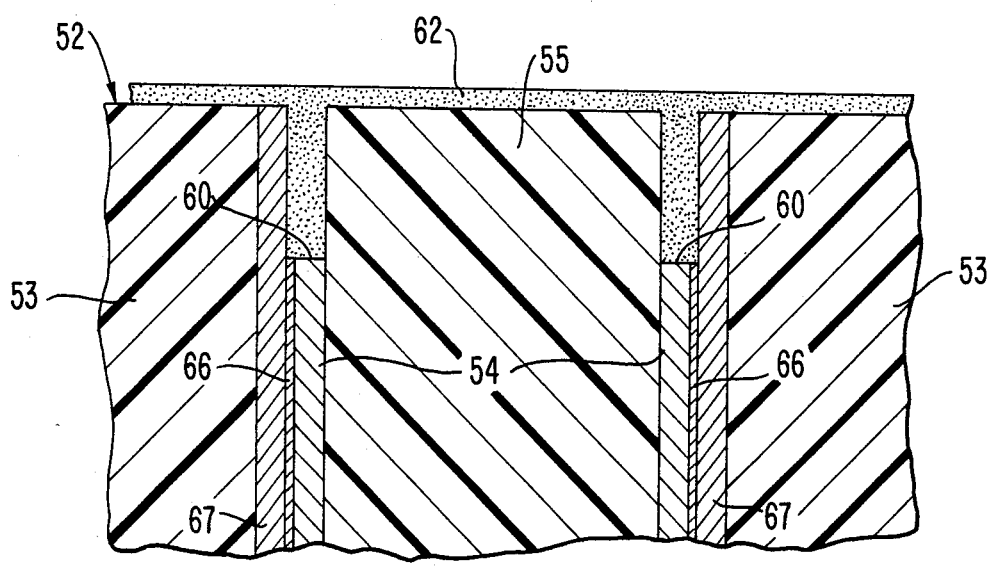
FIG. 6: An enlarged axial section through the measuring site in accordance with area 57 in FIG. 5.

Details of measuring site 213 can be seen in the magnified section diagram of FIG. 6.

The insulating body 55 is an elongated fiber, for example a quartz fiber. The electrode ring 54 is arranged on the cylindrical surface in the form of a metal film covering the length of the fiber up to its rear end where the electrode film may be contacted directly and connected to the cable 112.

On the film 54 which consists of a metal suitable for the present purposes, that is for pO$_2$-polarography, a chromium coating 66 is arranged.

An insulator layer 67 follows. With this layer construction, the chromium coating 66 provides for gapfree sealing towards the insulator layer 67. When applying polarographic potentials in the presence of water chemical corrosion is prevented by passivation of the chromium coating. The polarographic data of the measuring site therefore remain constant even during extended measurements.

The described arrangement including the insulating layer 67 is arranged within the steel tube 51 and fixed by means of the highly insulating casting compound 53. Subsequently, the surface 52 (FIG. 5) is ground. The intersection of the electrode film 54 with the precision ground surface 52 then forms the electrode ring illustrated in FIG. 5. A diffusion membrane 62 which can be seen in FIG. 6 has to be attached to the upper part of the arrangement in order to get a polarographic measuring site.

The diameter of the electrode ring or film 54—the actual measuring site—preferably is small and amounts to about the dimension range of micro probes, that is to 1 $\mu$m or less. The remaining probe diameter is largely necessary for the improvement of mechanical stability. However, the ring diameter may be larger by orders of magnitude as can be seen from FIG. 5. By means of selecting the thickness of the electrode film 54 accordingly, its free polarographic front surface can be made so small that the polarographic current is kept low. Thus, a low oxygen consumption and therefore a small stirring-effect dependence are achieved. The diffusion membrane 62 can be kept thin. Short diffusion paths and a short response time, that is a small $\tau_\nu$, are the result.

FIG. 6 shows that with the preferred embodiment the polarographic front area 60 of the electrode film 54 is withdrawn from the precision ground surface 52. A recess is formed between the ring area 60 and the precision ground surface 52, which is filled with membrane material when attaching the membrane 62.

The recess can be manufactured by etching the metal film 54. A first advantage is the fact that the etching makes the surface 60 smoother and especially smaller. Film sections that are perhaps protruding from the ground surface 52, enlarging the polarographic electrode surface, are eliminated. Thus deviations in the series-production are decreased and the polarographically active electrode surface is reduced.

A further advantage of the recess above the polarographically active front area 60 of the film 54 is that it reduces, in a geometrical way, the oxygen diffusion to the polarographic ring area. The membrane 62 can be further decreased to almost zero so that membrane material may be placed only in the recess.

It turned out that an optimum of the response time together with constant stirring effect can be achieved by means of varying the recess depth, that is the distance between the area 60 and precision ground surface 52. In this way extremely fast probes almost free of production deviations and with a low stirring effect can be built.

It was found that the optimum recess depth is within the order of magnitude of the thickness of the electrode film 54. The mentioned optimum of the response time at a sufficiently low stirring effect is given at a recess depth of about the 2.5-times the film thickness.

The field of application of the design of the measuring site in accordance with FIG. 6, especially having the recess, is not limited to probes for the previously described apparatus for the determination of pO$_2$-histograms. Such a kind of measuring site also can be used favorably for micro probes. This kind of measuring site is particularly suited for tissue surface probes being applied to the surface of organs for the determination of a pO$_2$-histogram by determining local pO$_2$-values on the organ surface by means of several measuring sites spread over the area. Several measuring sites of the present invention can be arranged in spaced relationship in a common molded body 53.

What is claimed is:

1. An apparatus for the construction of pO$_2$ histograms from measurements made in living tissue comprising the combination of a needle probe having a pO$_2$ measuring site near the tip of said probe at its distal end, the outer diameter of said probe adjacent said measuring site being greater than 10 microns;

incremental drive means for axially moving said needle probe in steps to successively position said measuring site at individual measuring locations separated from each other by a predetermined distance, said predetermined distance being greater than the distance between the measuring site and said probe tip plus a predetermined tissue—dependent amount in the order of magnitude of the diameter of said probe at said distal end, said drive means being operative to move said probe tip through said steps of said predetermined distance in a time which is less than an average time constant $\tau_g$ of the pO$_2$ decrease in the interstitial tissue after cutoff of the oxygen supply; and signal evaluation means for evaluating the measurement made at each location and producing a signal for display, said evaluation means and measuring site together having a response time constant $\tau_v$ to pO$_2$ changes which is at least 30 times smaller than said average time constant $\tau_g$, said signal evaluation means including means for producing a signal for display at a time which is between about $3\tau_v$ and about $0.1\tau_g$ after the end of each said step movement.

2. Apparatus according to claim 1, wherein the ratio $\tau_g/\tau_v$ is more than 100.

3. Apparatus according to claim 1, wherein the probe diameter in the distal area (211) is larger than about 100 microns.

4. Apparatus according to claim 1, wherein the measuring site (213) is fastened in the precision ground opening of a metal cannula.

5. Apparatus according to claim 1, having a polarographic measuring site, wherein the measuring site is formed as a precision ground surface (52) of a metal film (54) imbedded between insulating materials (55, 53) and covered by a diffusion-permeable membrane (62).

6. Apparatus according to claim 5, wherein the film (54) is arranged on a fiber core (55) and surrounded by a casting compound (53).

7. Apparatus according to claim 6, wherein the surface (60) of the metal film (54) is arranged below the precision ground surface (52) in a distance of the order of magnitude of the film thickness.

8. Apparatus according to claim 1 for determination within the skeletal muscles of a patient, wherein the probe diameter amounts to about 200 to 500 microns and the step distance to more than about 400 microns, $\tau_v$ being less than 150 milliseconds and the measured value being determined not later than 1.5 seconds after the termination of movement.

9. A method of making a plurality of measurement in living tissue for presentation in a pO$_2$ histogram including providing a needle probe having a pO$_2$ measuring site near its distal end and having a diameter greater than 10 microns, inserting the probe into the tissue and moving the measuring site axially and incrementally to successive measurement locations separated by distances greater than the distance between the measuring site and the probe tip plus a constant having a magnitude in the order of magnitude of the probe tip diameter and selected as a function of tissue characteristics, determining from the tissue characteristics an average time constant $\tau_g$ representative of the pO$_2$ decrease in the interstitial tissue after cutoff of the supply of oxygen thereto, moving the measuring site in the incremental movements from one measuring location to the next measuring location in a time which is less than the average time constant $\tau_g$ by at least an order of magnitude, making the pO$_2$ measurement at each location in an interval of time which is at least an order of magnitude smaller than the average time constant $\tau_g$, and displaying the measurements.

* * * * *